(12) United States Patent
Mathieu et al.

(10) Patent No.: US 8,216,283 B2
(45) Date of Patent: Jul. 10, 2012

(54) DEVICE FOR OSTEOSYNTHESIS

(75) Inventors: Claude Mathieu, Bettlach (CH); Robert Frigg, Bettlach (CH); Harald Saner, Selzach (CH)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 12/698,433

(22) Filed: Feb. 2, 2010

(65) Prior Publication Data

US 2010/0137867 A1 Jun. 3, 2010

Related U.S. Application Data

(63) Continuation of application No. 10/877,096, filed on Jun. 24, 2004, now Pat. No. 7,682,379, which is a continuation of application No. PCT/CH01/00740, filed on Dec. 24, 2001.

(51) Int. Cl.
*A61B 17/88* (2006.01)
(52) U.S. Cl. .................................................. 606/280
(58) Field of Classification Search .................. 606/280, 606/70, 71, 281–299, 309; 403/89
See application file for complete search history.

(56) References Cited

U.S. PATENT DOCUMENTS 6,030,389 A * 2/2000 Wagner et al. ................. 606/71
* cited by examiner

*Primary Examiner* — Eduardo C Robert
*Assistant Examiner* — Tara Carter
(74) *Attorney, Agent, or Firm* — Fay, Kaplun & Marcin, LLP

(57) ABSTRACT

The device for performing osteosynthesis includes a fixation element, such as a bone plate having a bottom surface designed to bear against the bone, a top surface, and at least one through hole extending from the bottom surface to the top surface, the though hole having a central axis and configured and dimensioned to receive a multiaxially pivotal insert or bushing for a bone screw. A bushing insertable into the through hole, includes a central bore designed to receive a bone screw, the central bore having a longitudinal axis, and a peripheral outer surface designed to be in contact with the through hole. The bushing is configured and dimensioned to be radially compressible and radially expansible, and the cross section of the through hole, which is orthogonal to the central axis, is non-circular. The cross section of the bushing that is orthogonal to the longitudinal axis has a shape that corresponds substantially to the cross section of the through hole of the bone plate. When placed in the through hole, the bushing is rotationally fixed relative to its longitudinal axis, but remains pivotally adjustable within the through hole relative to the bone plate.

9 Claims, 4 Drawing Sheets

DEVICE FOR OSTEOSYNTHESIS

RELATED APPLICATIONS

The present application is a Continuation of application of U.S. patent application Ser. No. 10/877,096 filed on Jun. 24, 2004 now U.S. Pat. No. 7,682,379 which is a continuation of the U.S. National Stage designation of co-pending International Patent Application No. PCT/CH01/00740, filed Dec. 24, 2001, the entire content of which is expressly incorporated herein by reference thereto.

FIELD OF THE INVENTION

The invention relates to a device for osteosynthesis, and more particularly, to a fixation device, such as a bone plate, having a polyaxial bushing and screw assembly for securing such a device to bone.

BACKGROUND OF THE INVENTION

Assemblies of the present type serve for screwing together elements such as pedicle screws or pedicle hooks in a polyaxial, rigid manner, and are used in particular in the area of the spinal column. However, these assemblies may also be employed for plating in general. Additional fields of application include use in combination with external fixators and intervertebral implants.

A device of this type is shown in U.S. Pat. No. 6,235,033, in which a screw head and the bore of the bone plate are held together by an angularly adjustable, annular bushing which is compressible and expansible by means of a slot so as to achieve an improved fastening of the screw in the plate. This known device, however, suffers from the disadvantage that the bushing used is of circular shape so that it may rotate together with the screw as the screw is screwed in, thus preventing it from becoming locked within the plate. The bushing may even turn around completely within the plate hole, so that the wrong side thereof faces upward (the inner cone tapering in the wrong direction). The present invention is intended to provide a remedy for this undesirable movement of the bushing relative to the bone plate.

It is accordingly an object of the present invention to provide a device for osteosynthesis in which the bone screws are polyaxially movable and lockable in an angularly stable manner relative to the bone plate without the need for any additional mechanical elements.

It should be emphasized that the discussion of the state of the art as set out above is merely intended to illustrate the background of the invention and does not mean that at the moment of filing the present application, or its priority application, the cited state of the art was actually published or otherwise publicly known.

SUMMARY OF THE INVENTION

According to the invention, this object is achieved by means of a device for osteosynthesis comprising a fixation element having a through hole designed to receive a multi-axially pivotal bushing for a bone screw, the through hole having a central axis and a non-circular cross-section extending orthogonally to the central axis; and a bushing insertable in said through hole, the bushing including a central bore designed to receive a bone screw, the bore having a longitudinal axis, and a peripheral outside surface configured and dimensioned to be in contact with at least a portion of the interior surface of the through hole. The bushing is configured and dimensioned to be radially compressible and radially expansible, and a cross section of the bushing extending orthogonally to the longitudinal axis of the bushing is shaped substantially the same as the cross section of the through hole such that when the bushing is inserted in the through hole, it is secured against rotation relative to its longitudinal axis while remaining pivotally adjustable relative to the fixation element.

As used herein, the term "non-circular" refers to any cross section deviating from an exactly circular shape, and refers in particular, but is not limited to, prismatic and elliptical cross sections.

One advantage achieved by the device of the present invention consists in the fact that the bushing can no longer turn about its own axis while the bone screw is screwed in. The turning of said bushing would in fact entail that no relative movement between the bushing and the screw would take place, and that the bushing would, therefore, not be expanded. Consequently, a locking of the screw would not be possible. A further advantage consists in the fact that, unlike the device disclosed in U.S. Pat. No. 6,235,033, an additional locking screw is unnecessary.

In one particular embodiment, the cross section of the through hole formed in the osteosynthetic device, which, in a preferred embodiment includes a bone plate, is polygonal, preferably hexagonal, so that said through hole has the form of a prism, preferably a hexagonal prism. In the case of the hexagonal embodiment, the bone screw may be simultaneously moved in three planes within the hexagonal through hole, making it possible to adjust and fix the screw at any desired angle. Said angle is only limited by the plate thickness and by the abutment of the bushing on the reduced cross section. It is of course also possible to use bone plates having a plurality of through holes.

In a further embodiment, the diameter of the central bore of the bushing tapers in one direction and the bore is preferably shaped in the form of a cone. This configuration permits the bushing to be spread apart by means of a corresponding counter cone. However, the bore formed in the bushing may also be realised in a circular cylindrical shape.

Preferably, the bore of the bushing is provided with an internal screw thread. This permits a locking of the bushing.

Extending orthogonally to the central axis, the cross section of the through hole formed in the osteosynthetic device, which is preferably realised as a bone plate, may also be of elliptical shape.

In a specific embodiment, the cross section of the through hole consists of two incomplete semicircles connected to one another by means of non-circular lines. In this case, the bushing is provided with two protrusions formed on its outer surface which may be inserted into the grooves formed in the through hole by the non-circular lines.

In order to be radially compressible and radially expansible, the bushing may be provided with a continuous slot preferably extending parallel to the longitudinal axis of the bushing. In an alternative embodiment, the bushing may also have a plurality of non-continuous slots preferably extending parallel to the longitudinal axis.

The surface of the bushing, preferably in the area of its peripheral, outer surface, is suitably roughened, e.g. by means of grit blasting. The through hole formed in the bone plate may correspondingly be roughened, e.g. by means of grit blasting. However, the surface of the bushing, preferably in the area of its peripheral, outside face, may also be provided with a macrostructured portion, e.g. in the form of peripheral ridges. The through hole may then be correspondingly provided with a macrostructured portion, e.g. in the form of peripheral ridges. The advantage of this configuration lies in the positive engagement between the bushing and the bone plate which is thus achievable.

In another specific embodiment, the through hole formed in the osteosynthetic device, which, in a preferred embodiment includes a bone plate, tapers towards the bottom surface and preferably also towards the top surface, thus resulting in reduced cross sections which prevent the bushing from falling out or from being pressed out. Suitably, the reduced cross section of the through hole and the compressibility of the bushing are selected adequately so that it is still possible to introduce the compressed bushing into the through hole.

The form of the peripheral outside face of the bushing is suitably convex, and preferably cylindrical.

Preferably, the osteosynthetic device—at least in the area of its through hole—and the bushing—at least in the area of its peripheral outside face—consist of different materials, preferably of materials differing from each other in hardness. The bushing may, for example, consist of a biocompatible plastic material and the osteosynthetic device (e.g. a bone plate) of a biocompatible metal. However, the bushing may also be made of metal and the device of a plastic material, preferably a reinforced plastic material. The different materials cause a plastic deformation of the surfaces and thus lead to a positive engagement.

The height of the bushing measured in the direction of its longitudinal axis should be inferior to the height of the through hole formed in the bone plate as measured in the direction of its central axis. The height of the bushing may be between 40 and 85 percent of the height of the through hole. In one specific embodiment, the height of the bushing may be between 45 and 65 percent of the height of the through hole.

The bone screws to be introduced into the bushing preferably have a conical screw head which is provided with an external screw thread. The advantage of this configuration is that the spreading and the locking of the bushing may thus be realised in a single step.

In the following, the invention and improvements of the invention will be illustrated in greater detail with reference to the partially diagrammatic representations of several embodiments. All the embodiments relate to an osteosynthetic device including a bone plate. Analogous applications for pedicle screws, pedicle hooks, external fixators, or intervertebral implants are also possible and within the scope of the present invention.

BRIEF DESCRIPTION OF THE DRAWINGS

The present invention will be understood and appreciated more fully from the following detailed description, taken in conjunction with the drawings in which.

DETAILED DESCRIPTION OF THE PREFERRED EMBODIMENTS

Figure 1:
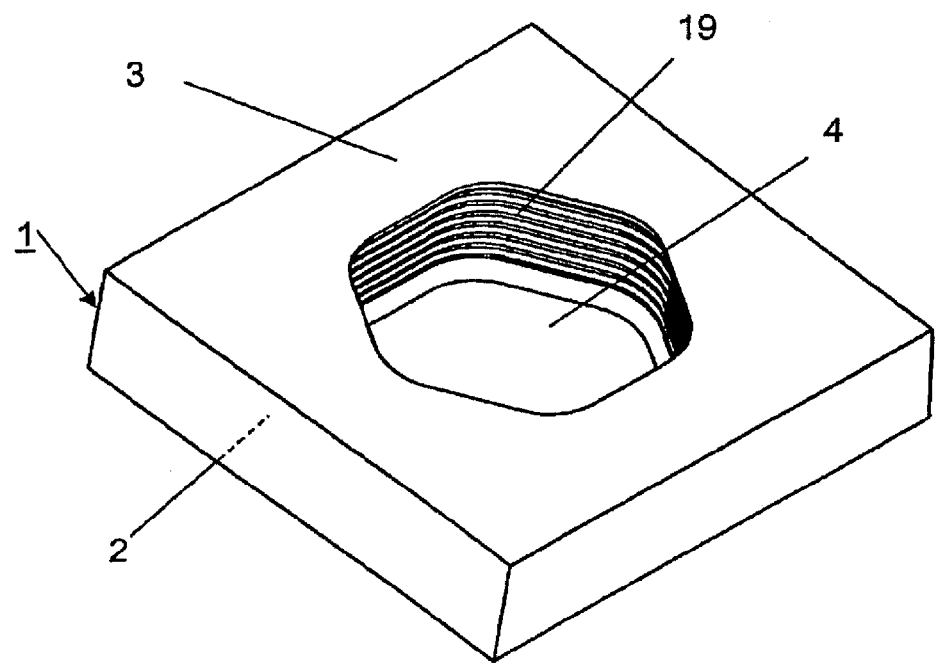
FIG. 1 is a perspective view of a fixation element according to a preferred embodiment of the present invention, wherein the fixation element is a bone plate.

The device for osteosynthesis represented in FIGS. 1 to 4 consists of a bone plate 1 including a bottom surface 2 designed to bear against the bone, a top surface 3, and a through hole 4 connecting the bottom surface 2 with the top surface 3, designed to receive a multiaxially adjustable bushing 10 for a bone screw 20 (FIG. 8), the through hole 4 having a central axis 5. The bushing 10 (FIG. 3) insertable into the through hole 4 includes a central bore 11 designed to receive the bone screw 20 (FIG. 8), the bore 11 having a longitudinal axis 12, as well as a peripheral outside face 17 designed to be in contact with the through hole 4.

The bushing 10 has a continuous slot 13 so as to be radially compressible and radially expansible. The through hole 4 of the bone plate 1 is provided, toward the bottom surface 2 and toward the top surface 3 thereof, with a reduced cross section 9 so as to prevent the bushing 10 from falling out or from being pressed out. Suitably, the reduced cross-section 9 of the through hole 4 and the compressibility of the bushing 10 are selected adequately so that it is still possible to introduce the compressed bushing 10 into the through hole 4.

Figure 2:
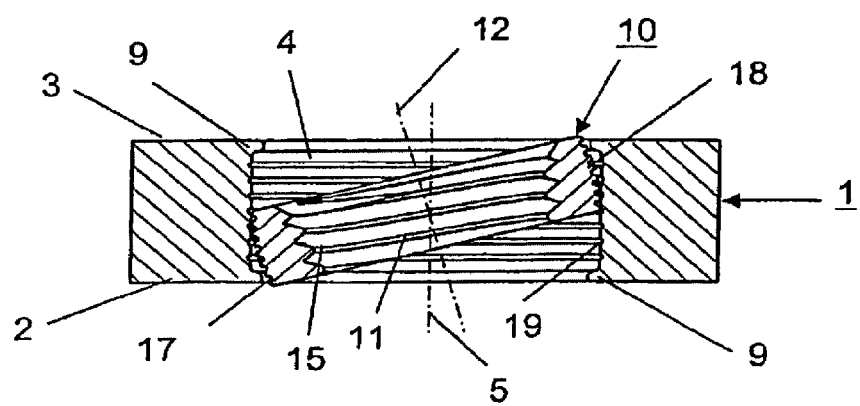
FIG. 2 is a cross section of the bone plate according to FIG. 1 with a bushing introduced therein.
Figure 3:
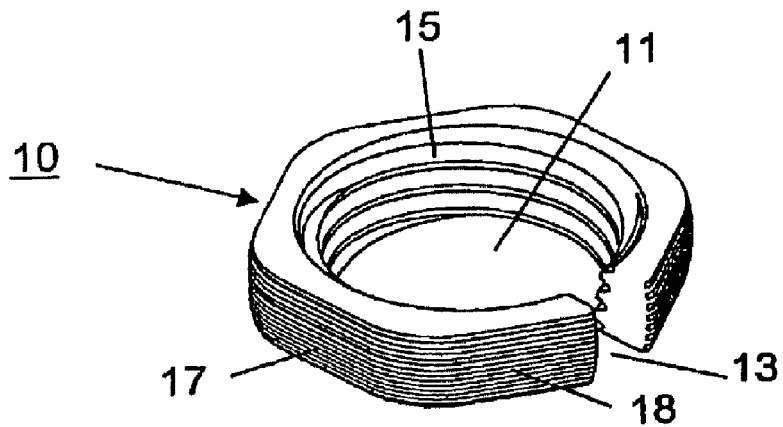
FIG. 3 is a perspective view of a bushing according to a preferred embodiment of the present invention.

As shown in FIG. 3, the surface of the bushing 10 is provided, in the area of its peripheral, outside face, with a macrostructured portion in the form of peripheral ridges 18. Correspondingly, the through hole 4 of the bone plate 1 is provided with a macrostructured portion in the form of peripheral ridges 19 (FIG. 2).

Figure 4:
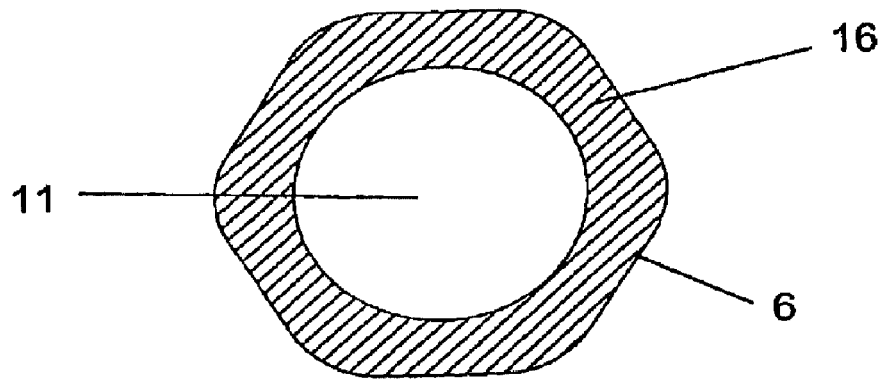
FIG. 4 is a horizontal cross section of the bushing shown in FIG. 3.

As shown in FIG. 4, the cross section 6 of the through hole 4 extending orthogonally to the central axis 5 is shaped in an approximately hexagonal, i.e. non-circular form. The cross section 16 of the bushing 10 extending orthogonally to the longitudinal axis 12 has a form corresponding substantially to that of the cross section 6 of the through hole 4 of the bone plate 1, so that the bushing 10 which is placed in the through hole 4 is rotationally stable relative to its longitudinal axis 12, while remaining adjustable within the through hole 4 as to its angular orientation relative to the bone plate 1.

As shown in FIG. 2, the diameter of the bore 11 tapers in the direction of the bottom surface 2 of the bone plate 1, so that the bore 11 has a conical shape. In addition, the bore 11 is provided with an internal screw thread 15.

Figure 5:
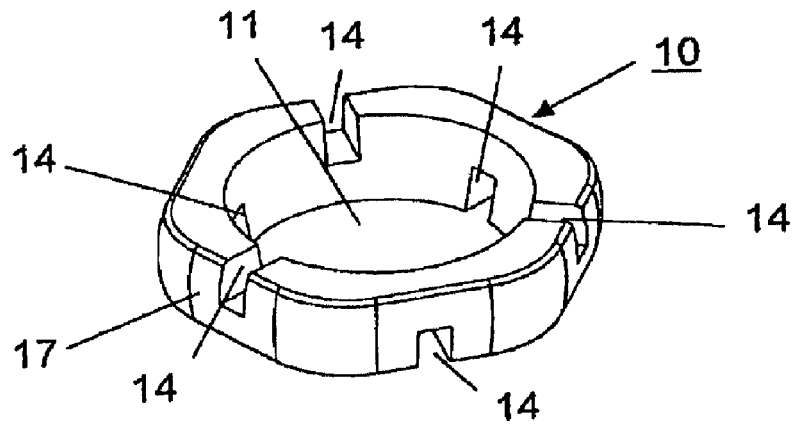
FIG. 5 is a perspective view of a bushing according to another preferred embodiment of present invention.

FIG. 5 shows another embodiment of the bushing 10 which comprises a plurality of non-continuous slots 14 extending parallel to the longitudinal axis 12. This permits the bushing 10 to be radially compressible and radially expansible without having a continuous slot.

Figure 6:
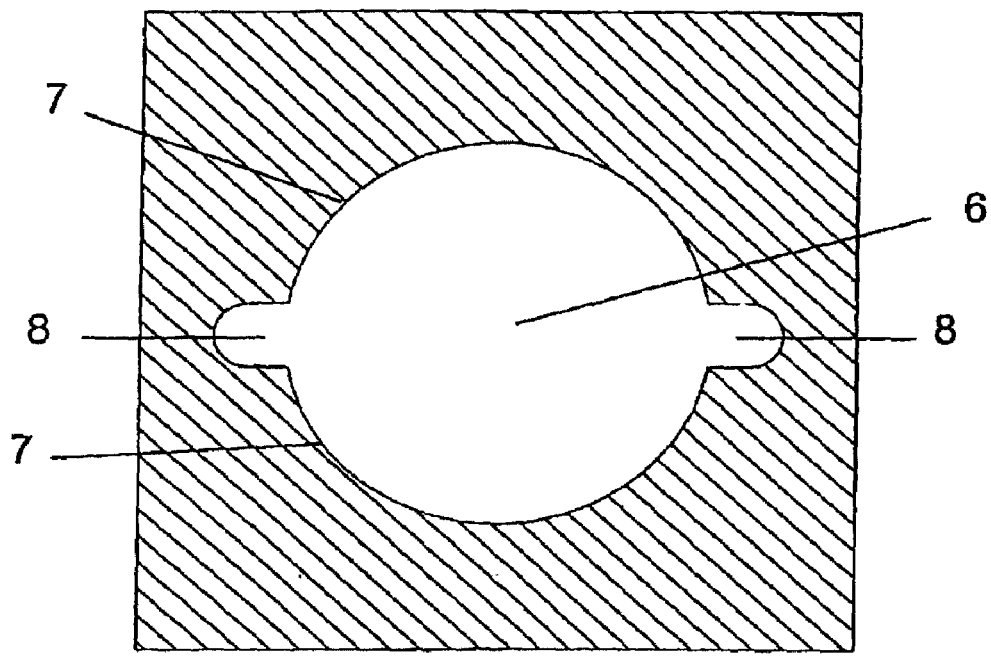
FIG. 6 is a horizontal cross section of another variation of a bone plate according to the present invention.
Figure 7:
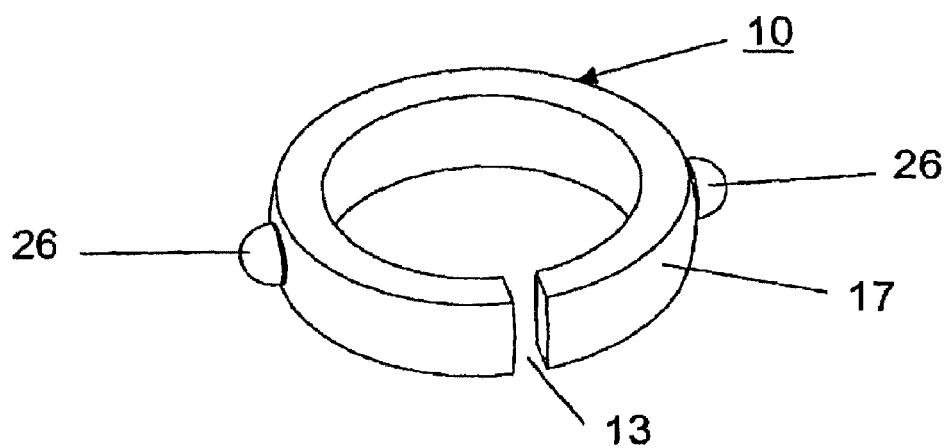
FIG. 7 is a perspective view of a bushing according to another preferred embodiment of the present invention, which mates with the bone plate according to FIG. 6.

FIGS. 6 and 7 show another embodiment of the bushing 10 and of the corresponding bone plate 1 in which the cross section 6 of the through hole 4 is defined by two incomplete semicircles 7 connected to each other by means of two non-circular lines 8. Corresponding to this, the bushing represented in FIG. 7 is shaped in the form of a ring the peripheral outside face 17 of which is spherical and which is provided with two diametrically opposed semicircular protrusions 26. The two protrusions 26 are received by the grooves formed by the non-circular lines 8 within the through hole 4 of the bone plate 1, which is equally spherical. When inserted into the bone plate, the bushing 10 is rotatable both about the two protrusions 26 and orthogonally to this axis of rotation, so that adjusting movements are possible in all directions apart from a movement in the plane of the plate (cardan joint).

Figure 8:
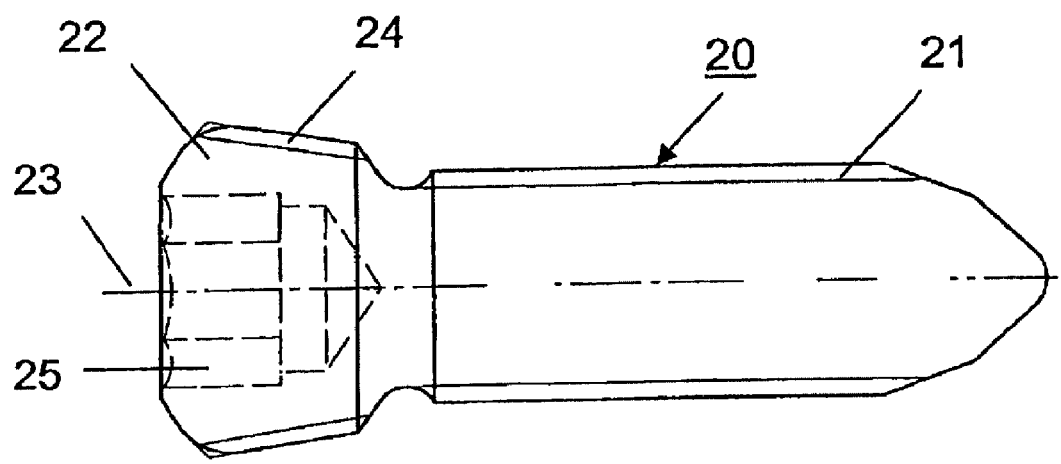
FIG. 8 is a longitudinal section of a bone screw to be used with a device for osteosynthesis according to the present invention.

The bushing 10 may receive the bone screw 20 represented in FIG. 8. The bone screw 20 has a threaded shaft 21 permitting it to be anchored within the bone, a screw axis 23, and a screw head 22 for insertion into the central bore 11 of the bushing 10, which corresponds substantially to the shape of the bore 11. The cross section of the screw head 22, which extends orthogonally to the screw axis 23, has a tapered portion proximal to the screw shaft 21, thus forming a cone. The screw head 22 is provided with an external screw thread 24 which corresponds to the internal screw thread 15 of the bushing 10. In addition, the screw head 22 is provided with a hexagon socket 15 for receiving an Allen key (not shown in the drawing).

In the following, the clinical utilization of the device for osteosynthesis will shortly be described.

The bushing 10 of the device comes preassembled in the bone plate 1 or in the jaw. It therefore does not need to be inserted by the surgeon. The bone plate with the preassembled bushings is applied to the bone. This may be done either before or after the reduction of the different bone fragments or vertebral bodies. There are three possible scenarios for placing the bone screws: a) drilling, tapping, screwing; b) drilling, screwing (using self-tapping screws); or c) screwing (using self-drilling and self-tapping screws).

It is also possible to use aiming devices or drill bushings. It is of course not suitable to use fixed aiming devices, as this would typically negate the advantage of an angularly adjustable screw, but such an aiming device may nonetheless make sense in cases in which a limitation of the range of adjustment is desirable. Drill bushings are needed in cases in which no self-drilling screws are used and a hole must be drilled prior to inserting the screw. In such cases the drill bushing serves to prevent soft-tissue injury.

There are basically two possible ways of placing a plurality of bone screws:

A) if bone reduction is done prior to the application of the plate, the screws may immediately be fastened; and B) in cases in which bone reduction is done after the application of the plate, the screws are first turned in only so far as to fix the plate on the bone; after that, the final bone reduction or correction takes place and the screws are subsequently turned in a few more angular degrees so as to become locked within the plate.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

What is claimed is:

1. A device for osteosynthesis, comprising:
   a fixation element having a through hole having a central axis and a cross section that extends orthogonally to the central axis and is one of at least partially polygonal, at least partially prismatic, and at least partially elliptical; and
   a bushing insertable in said through hole, the bushing including a central bore structured to receive a bone fixation element, wherein a cross section of the bushing extending orthogonally to a longitudinal axis of the bushing is shaped substantially the same as the cross section of the through hole such that when the bushing is inserted in the through hole, it is secured against rotation about its longitudinal axis.

2. The device of claim 1, wherein the cross section of the through hole is hexagonally shaped.

3. The device of claim 1, wherein the through hole of the fixation element is prismatically shaped.

4. The device of claim 3, wherein the through hole of the fixation element is shaped as a hexagonal prism.

5. The device of claim 1, wherein the bore of the bushing tapers in one direction.

6. The device of claim 1, wherein the bore of the bushing has a conical shape.

7. The device of claim 1, wherein the bore of the bushing has a cylindrical shape.

8. The device of claim 1, wherein the bore of the bushing has an internal thread.

9. The device of claim 1, wherein the bushing has a continuous slot.

* * * * *